US012275950B2

(12) United States Patent
Jurk et al.

(10) Patent No.: US 12,275,950 B2
(45) Date of Patent: Apr. 15, 2025

(54) IN VITRO METHOD OF REPROGRAMMING FIBROBLAST CELLS INTO INDUCED PLURIPOTENT STEM CELLS BY TRANSCRIPTION FACTORS MRNAS CO-TRANSFECTED WITH SOCS1 MRNA WHEREIN THE MRNAS HAVE A POLY-A TAIL OF AT LEAST 2000 ADENINES

(71) Applicant: Miltenyi Biotec GmbH, Bergisch Gladbach (DE)

(72) Inventors: Marion Jurk, Pulheim (DE); Stefan Wild, Cologne (DE); Andreas Bosio, Cologne (DE)

(73) Assignee: MILTENYI BIOTEC B.V. & CO. KG, Bergisch Gladbach (DE)

( * ) Notice: Subject to any disclaimer, the term of this patent is extended or adjusted under 35 U.S.C. 154(b) by 543 days.

(21) Appl. No.: 16/099,134

(22) PCT Filed: May 2, 2017

(86) PCT No.: PCT/EP2017/060345
§ 371 (c)(1),
(2) Date: Nov. 5, 2018

(87) PCT Pub. No.: WO2017/191096
PCT Pub. Date: Nov. 9, 2017

(65) Prior Publication Data
US 2019/0144886 A1 May 16, 2019

(30) Foreign Application Priority Data
May 6, 2016 (EP) .................................... 16168589

(51) Int. Cl.
C12N 15/00 (2006.01)
C07K 14/47 (2006.01)
C12N 5/07 (2010.01)
C12N 5/074 (2010.01)
C12N 5/0775 (2010.01)
C12N 5/0783 (2010.01)
C12N 5/0789 (2010.01)
C12N 5/10 (2006.01)
C12N 15/87 (2006.01)

(52) U.S. Cl.
CPC .......... *C12N 15/87* (2013.01); *C07K 14/4703* (2013.01); *C12N 5/0636* (2013.01); *C12N 5/0662* (2013.01); *C12N 5/0696* (2013.01); *C12N 5/10* (2013.01)

(58) Field of Classification Search
CPC ...... C12N 15/85; C12N 15/87; C12N 5/0696; C12N 2501/602; C12N 2501/603; C12N 2501/604; C12N 2501/606; C12N 5/602; A61K 2039/515
See application file for complete search history.

(56) References Cited

U.S. PATENT DOCUMENTS

| 9,012,219 | B2 * | 4/2015 | Kariko | ............... | A61K 48/0041 |
| | | | | | 435/377 |
| 9,597,380 | B2 * | 3/2017 | Chakraborty | .......... | C12N 15/67 |
| 9,701,965 | B2 * | 7/2017 | Schrum | .................. | C07H 21/02 |
| 9,862,926 | B2 * | 1/2018 | Chin | .................... | C12N 5/0658 |
| 2011/0143397 | A1 * | 6/2011 | Kariko | ............... | C07K 14/4712 |
| | | | | | 435/70.3 |

FOREIGN PATENT DOCUMENTS

| WO | WO2009072003 A2 | 6/2009 |
| WO | WO2009072003 A3 | 6/2009 |
| WO | WO2013003475 A1 | 1/2013 |

OTHER PUBLICATIONS

Cittadini et al. Cardiovas. Res. 2012; 96:381-390.*
Kinjyo et al., Immunity 2002; 17:583-591.*
Piganis et al., J. Biol. Chem. 2011; 286:33811-33818.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Alberts et al., Innate Immunity, Book: Mol. Biol of the Cell, 4th edition. New York, Garland Science 2002.*
Alcami, A. et al. (Dec. 2000, "The Vaccinia Virus Soluble Alpha/Beta Interferon (IFN) Receptor Binds to the Cell Surface and Protects Cells from the Antiviral Effects of IFN," Journal of Virology 74(23):11230-11239.
De Sepulveda, P. et al. (Feb. 15, 1999). Socs1 Binds to Multiple Signalling Proteins and Suppresses Steel Factor-Dependent Proliferation, The EMBO Journal 18(4):904-915.
Hajnsdorf, E et al. (Feb. 15, 2000). "Host factor Hfq of *Escherichia coli* Stimulateselongation of Poly(A) Tails by Poly(A) Polymerase I," Proc. Natl. Acad. Sci. USA 15;97(4):1501-1505.

(Continued)

Primary Examiner — Chang-Yu Wang
(74) Attorney, Agent, or Firm — Morrison & Foerster LLP

(57) ABSTRACT

The present invention provides the use of a nucleic acid encoding SOCS1 for enhancing the efficacy of introducing at least one nucleic acid of interest into a cell; a method of repeated transfection of a cell with at least one nucleic acid of interest comprising the steps of adding a) nucleic acid encoding SOCS1, and simultaneously or subsequently b) at least one nucleic acid of interest encoding at least one polypeptide of interest, wherein at least step b) is repeated at least once; and a method of electroporation of a cell with at least one nucleic acid of interest comprising the steps of adding to the cell a) a nucleic acid encoding SOCS1, and simultaneously or subsequently b) said at least one nucleic of interest. The at least one nucleic acid of interest and the nucleic acid encoding SOCS1 may be mRNAs, wherein each of said mRNAs has a poly(A) tail at its 3' end comprising at least 200 adenines.

5 Claims, 6 Drawing Sheets

(56) References Cited

OTHER PUBLICATIONS

He, C. et al. (Aug. 2015). "Topical administration of a Suppressor of Cytokine Signaling-1 (SOCS1) Mimetic Peptide Inhibits Ocular Inflammation and Mitigates Ocular Pathology During Mouse Uveitis," J. Autoimmun. 62:31-38, 18 pages.

Hong, X-X. et al. (May 31, 2013, e-pub. Apr. 18, 2013). "Innate Immunity in Pluripotent Human Cells. Attenuated Response To Interferon-β," The Journal Of Biological Chemistry 288(22):16196-16205.

Jalkanen, A.L. et al. (Oct. 2014). "Determinants and Implications of mRNA Poly(A) Tail Size—Does this Protein Make My Tail Look Big?," Semin Cell Dev Biol. 34:24-32.

Kariko, K. et al. (Aug. 2005). "Suppression of RNA Recognition by Toll-like Receptors: The Impact of Nucleoside Modification and the Evolutionary Origin of RNA," Immunity 23(2):165-175.

Liang, Y. et al. (2014). "SOCS Signaling in Autoimmune Diseases: Molecular Mechanisms and Therapeutic Implications," Eur. J. Immunol. 44:1265-1275.

Poleganov, M.A. et al. (Nov. 1, 2015). "Efficient Reprogramming of Human Fibroblasts and Blood-Derived Endothelial Progenitor Cells Using Nonmodified RNA for Reprogramming and Immune Evasion", Human Gene Therapy 26(11):751-766.

Preiss, T. et al. (1998). "Poly(A)-Tail-Promoted Translation in Yeast: Implications for Translational Control," RNA 4(11):1321-1331.

Warren, L. et al. (Sep. 14, 2012). "Feeder-Free Derivation of Human Induced Pluripotent Stem Cells with Messenger RNA," Scientific Reports 2(657):1-7.

Hebenstreit, D. et al. (2005, e-pub. Nov. 11, 2004). "SOCS-1 and SOCS-3 Inhibit IL-4 and IL-13 Induced Activation of Eotaxin-3/CCL26 Gene Expression in HEK293 Cells," Molecular Immunology 42:295-303.

Dreyfus, M. et al. (Nov. 27, 2002). "The Poly(A) Tail of mRNAs: Bodyguard in Eukoaryotes, Scavenger in Bacteria," Cell 111:611-613.

Schlee, M. et al. (2016, e-pub. Jul. 25, 2016). "Discriminating Self From Non-Self in Nucleic Acid Sensing," Nature 16:566-580.

Semenova, N. et al. (2019, e-pub. Sep. 9, 2014). "Multiple Cytosolic DNA Sensors Bind Plasmid DNA After Transfection," Nucleic Acids Research 47(49):10235-10246.

Sundaran, K. et al. (2013). "SOCS-1/3 Participation in FGF-2 Signaling to Modulate RANK Ligand Expression in Paget's Disease of Bone," Journal of Cellular Biochemistry 114:2032-2038.

Zhongle, C. et al. (Mar. 2011). "Effect of SOCS1 on the Antiviral Replication of Interferon-α," Acta Universitatis Medicinalis Anhui 46(3):228-230. (Translation of the Abstract on p. 230).

Brouwer, M. et al. (Feb. 2016, e-pub. Oct. 1, 2015). "Choices for Induction of Pluripotency: Recent Developments in Human Induced Pluripotent Stem Cell Reprogramming Strategies," Stem Cell Rev Rep. 12(1):54-72.

Warren, L. et al. (Nov. 5, 2010, e-pub. Sep. 30, 2010). "Highly Efficient Reprogramming To Pluripotency And Directed Differentiation Of Human Cells With Synthetic Modified mRNA," Cell Stem Cell. 7(5):618-630, 14 pages.

Xiao, T. (2009, e-pub. Apr. 4, 2012). "Innate Immune Recognition Of Nucleic Acids," Immunol. Res. 43(1-3):98-108, 12 pages.

Wu, J. et al. (2014). "Innate Immune Sensing and Signaling of Cytosolic Nucleic Acids," Annu. Rev. Immunol. 32:461-488.

* cited by examiner

IN VITRO METHOD OF REPROGRAMMING FIBROBLAST CELLS INTO INDUCED PLURIPOTENT STEM CELLS BY TRANSCRIPTION FACTORS MRNAS CO-TRANSFECTED WITH SOCS1 MRNA WHEREIN THE MRNAS HAVE A POLY-A TAIL OF AT LEAST 2000 ADENINES

CROSS-REFERENCE TO RELATED APPLICATIONS

This application is a National Phase filing under 35 U.S.C. § 371 of International Application No.: PCT/EP2017/060345, filed on May 2, 2017, which claims priority benefit to EP Application Ser. No. 16/168,589.6, filed on May 6, 2016.

BACKGROUND

Transfection of nucleic acids, e.g. DNA or RNA, triggers a so called innate immunity in cells. Cytoplasmatic proteins recognize non-self nucleic acids and activate signal transduction pathways resulting among others in production of cytokines and may lead to apoptosis of the cell. One signaling pathway which is triggered is the interferon (IFN) signal transduction pathway. Such effects are not important for the survival of the cell if the cells are transfected once. But a strongly increased death of the cells is observed if the cells have to be transfected repeatedly within several days. Regularly, this leads to cell death of the transfected cells.

The vaccinia virus soluble alpha/beta interferon receptor (B18R) binds to the cell surface and protects cells from the antiviral effects of IFN (Alcami et al, 2000, Journal of Virology, 74:11230-11239). Addition of the protein B18R protein to cell media after repeated transfection of cells results in a strongly decreased death of cells and in an increased expression of the transfected gene. B18R protein, for example, is added to a cell medium after daily performed transfection of cells for the reprogramming of primary, differentiated cells to induced pluripotent stem cells (iPSCs) by means of mRNAs of reprogramming factors (Warren et al. 2012, SCIENTIFIC REPORTS 2: 657, DOI: 10.1038/srep00657). B18R is added as a protein to the medium and therefore has the disadvantage of a laborious and expensive production. Often purified proteins still are contaminated with unwanted components such as endotoxins which cannot be separated from the protein or only with immense effort. In addition, proteins prepared for adding to another environment such as a cell culture medium often cause trouble in estimating the real concentration in the new environment as proteins often have hydrophobic areas which stick to the wall of the vessels harboring the protein.

Poleganov et al. (Hum Gene Ther 2015, 26 (11), 751-66) report a combination of various viral mRNAs (Vaccinia virus derived mRNAs of B18R, E3 and K3) to rescue the cells from the unwanted effects of activation of the innate immunity. When combined with reprogramming-associated microRNAs (miRNAs), this results in an feeder-free iPS cell generation method. The disadvantage of this method is the rather complex mRNA/miRNA cocktail which is necessary for promoting reprogramming.

In Hong and Carmichael (2013, THE JOURNAL OF BIOLOGICAL CHEMISTRY, 288: 16196-16205) it is shown that an attenuated cellular response to type I IFNs may be a general feature of pluripotent human stem cells and that this is associated with high expression of suppressor of cytokine signaling 1 (SOCS1).

It has been described that most mRNAs within a cell have poly(A) length of 50 to 150 nucleotides (Jalkanen, A L et al., Semin Cell Dev Biol. 2014; 34:24-32.).

Therefore, the general assumption is that for mRNAs produced in vitro, poly-A tails resembling the length found in cells should be used. Whereas very short poly-A tails are associated with faster degradation, it has been shown that translation efficiencies of mRNA increases with poly-A length in a range of 15 to 98 adenosines (Preiss, T et al., RNA. 1998; 4(11):1321-31). Typically, poly-A tail lengths for in vitro transcribed mRNAs are in a range of 20 to 200 nucleotides. In the above-mentioned publication by Poleganov et al all mRNAs contained a poly A tail of exactly 120 A.

E. coli poly(A) polymerase, the most common enzyme to polyadenylate RNA in vitro, has been described to give poly-A tails of only 20-150 nucleotides. When combined with Hfq protein, of up to 900 nucleotides have been described (Hajnsdorf E et al., Proc Natl Acad Sci USA. 2000, 15; 97(4):1501-5.). Few poly(A) polymerases are able to generate longer poly(A) tails, e.g. yeast poly(A) polymerase.

There is a need in the art for an improved or alternative method for introducing nucleic acid molecules of interest into a cell which reduces the unwanted effects of the so called innate immunity of the cells which can occur by introducing nucleic acids into a cell.

SUMMARY OF INVENTION

Surprisingly it was found that a nucleic acid encoding SOCS1 such as SOCS1 mRNA can be used with beneficial effects for the expression of a nucleic acid of interest encoding a polypeptide of interest in a cell (for example in a cell culture medium) which is co-introduced (e.g. by transfection or electroporation) with said nucleic acid encoding SOCS1 such as SOCS1 mRNA. It was completely unexpected that a nucleic acid encoding SOCS1 such as SOCS1 mRNA can be used for repeated transfection processes as well as for an electroporation process to achieve the beneficial effects for the expression of the co-introduced nucleic acid(s) of interest. The introduction of said nucleic acid encoding SOCS1 into a cell reduces the effects of the so called innate immunity of cells, thereby improving cell survival and/or improving expression of a co-introduced nucleic acid of interest in the cell compared to a cell in which the nucleic acid encoding SOCS1 was not co-introduced. The introduction of said nucleic acid encoding SOCS1 such as SOCS1 mRNA into a cell reduces the effects of the innate immunity of cells by promoting cell survival due to attenuating the type I IFN response of a cell. Normally, especially repeated transfection of nucleic acids triggers the innate immunity in cells which subsequently may lead to apoptosis of the cell. Therefore, it is completely unexpected that a sole nucleic acid encoding SOCS1 such as SOCS1 mRNA used e.g. in a cell culture medium for repeated transfection of a cell escapes this fate and can assist other nucleic acids which are co-transfected to become expressed in the transfected cell. Again, the expression of SOCS1 in the transfected cell attenuates the cellular response to type I IFNs which normally may lead to apoptosis, thereby reducing the effects of the innate immunity of the cells. Other nucleic acids such as B18R mRNA alone did not show this beneficial effect although B18R protein (as a gold standard in the prior art) is added to a cell medium after daily performed transfection of cells for the reprogramming of primary, differentiated cells to induced pluripotent stem cells. As mentioned above on the level of nucleic acids until now only a combination of various viral mRNAs have been shown to rescue the cells from the unwanted effects of activation of the innate immunity. Surprisingly we identified that one nucleic acid, i.e. a nucleic acid encoding SOCS1, preferentially SOCS1 mRNA introduced into a cell is sufficient to avoid or reduce the effects of activation of innate immunity.

The nucleic acid encoding SOCS1 such as SOCS1 mRNA as agent within a transfection process (e.g. in a cell culture medium) for reducing the effects of the innate immunity of cells in a repeatedly transfected cell has the benefit of being a nucleic acid, which does nor harbor the above-mentioned disadvantages of a protein such as B18R. Especially, the production of a nucleic acid such as an mRNA and its purification is easier compared to a protein. The nucleic acid encoding SOCS1 such as SOCS1 mRNA as agent (e.g. in a cell culture medium) for reducing the effects of the innate immunity of cells in a repeatedly transfected cell has also the benefit of being one nucleic acid only compared to the combination of various viral mRNAs ("a cocktail") which have been shown in the art to rescue the cells from the unwanted effects of activation of the innate immunity.

The nucleic acid encoding SOCS1 and the at least one nucleic acid of interest encoding a polypeptide of interest which are added to the cell (e.g. by adding the said nucleic acids to a medium harboring the cell to be transfected) simultaneously or subsequently may be DNA molecules which are transcribed into mRNAs and subsequently translated into polypeptides, so they can exert the above-described effects. Alternatively, the nucleic acid encoding SOCS1 may be a SOCS1 mRNA molecule and the nucleic acids of interests may be either DNA or RNA. Preferentially, both the nucleic acid encoding SOCS1 and the nucleic acid(s) of interest encoding polypeptide(s) of interests may be mRNA molecules.

In addition surprisingly it was found that the longer the poly(A) tail of the mRNAs (both the SOCS1 mRNA and the mRNA encoding polypeptides of interest) the better the transfection efficacy and/or the level of expression of the polypeptide(s) of interest encoding by the nucleic acid(s) of interest. This means that the longer the poly(A) tail of the mRNAs the more repeated transfections of the same cell is possible. Therefore, preferentially, the mRNA used in the present method has a poly(A) tail at its 3' end comprising at least 200 adenines, more preferentially at least 1500 adenines, even more preferentially at least 2000 adenines and most preferentially at least 4000 adenines. Such long poly(A) tails can be generated by e.g. yeast poly(A) polymerase.

As long as the nucleic acid encoding SOCS1 is present in the transfected cell (i.e. it is translated into a polypeptide), achieved e.g. by the first co-transfection of the nucleic acid encoding SOCS1 and the at least one nucleic acid of interest, it is sufficient for a repeated transfection (or for several repeated transfections) of the same cell to transfect said cell with said at least one nucleic acid of interest.

Even more unexpectedly, it was found that unmodified or only slightly modified mRNA of the nucleic acid encoding SOCS1 and of the nucleic acid(s) of interest used in the methods of the present invention is even better than the modified or stronger modified variants of said nucleic mRNAs (e.g. 100% of the nucleobases uracil and/or cytosine are modified nucleobases). This is surprising because regularly rather strongly modified mRNA of gene(s) of interests are used to achieve a more stable mRNA molecule for transfection and the activation of innate immune responses is much more pronounced by unmodified mRNA (Kariko et al. Immunity 2005, 23 (2), 165-175).

In addition surprisingly, it was found that the nucleic acid encoding SOCS1 can also be used in a method of electroporation of a cell with at least one nucleic acid of interest (e.g. in a cell culture medium) resulting in improve survival of the cells and/or resulting in more cells expressing the nucleic acid molecule(s) of interest in the cell.

DETAILED DESCRIPTION OF THE INVENTION

Figure 1:
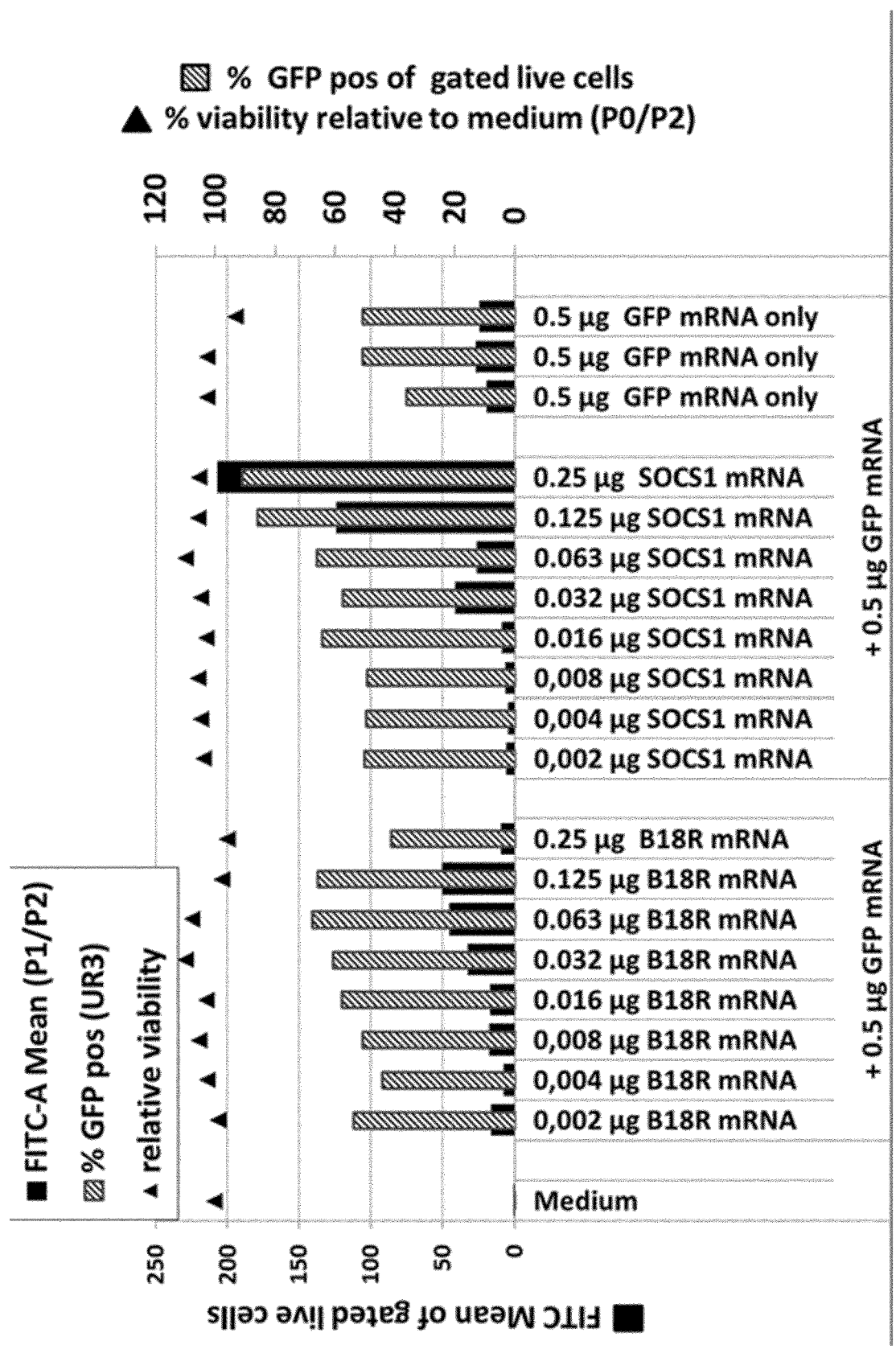
FIG. 1: Flow cytometric determination of the intensity of GFP mRNA expression in human fibroblasts after 3 consecutive, daily transfections.

In one aspect the invention provides the use of a nucleic acid encoding SOCS1 for enhancing the efficacy of introducing at least one nucleic acid of interest into a cell and/or for improved survival of a cell into which at least one nucleic acid of interest is introduced.

Said nucleic acid encoding SOCS1 may be mRNA and may have a poly(A) tail at its 3'end comprising at least 200 adenines, at least 500 adenines, at least 1000 adenines, at least 1500 adenines, at least 2000 adenines, at least 2500 adenines, at least 3000 adenines, at least 3500 adenines, at least 4000 adenines, at least 4500 adenines, at least 4500 adenines, at least 5000 adenines, at least 5500 adenines or at least 6000 adenines.

Said at least one nucleic acid of interest may be DNA.

Said at least one nucleic acid of interest may be mRNA and may have a poly(A) tail at its 3'end comprising at least 200 adenines, at least 500 adenines, at least 1000 adenines, at least 1500 adenines, at least 2000 adenines, at least 2500 adenines, at least 3000 adenines, at least 3500 adenines, at least 4000 adenines, at least 4500 adenines, at least 4500 adenines, at least 5000 adenines, at least 5500 adenines or at least 6000 adenines.

The use of said nucleic acid encoding SOCS1 for enhancing the efficacy of introducing at least one nucleic acid of interest into a cell is disclosed in more detail in the following sections.

In one aspect the invention provides a method of repeated transfection of a cell with at least one nucleic acid of interest, e.g. in a cell culture medium, comprising the steps of adding to the cell
  a) a nucleic acid encoding SOCS1; and simultaneously or subsequently
  b) said at least one nucleic acid of interest encoding at least one polypeptide of interest;
wherein at least step b) is repeated at least once.

Step a) may be also repeated every time when step b) is repeated, alternatively step a) may be repeated at least every second, third, fourth, fifth, sixth, seventh or eighth time when step b) is repeated.

In one embodiment of the invention, when step a) is also repeated every time when step b) is repeated, then the invention provides a method of repeated transfection of a cell with at least one nucleic acid of interest, e.g. in a cell culture medium, comprising the steps of adding to the cell (or to the medium if the cell is in a cell medium)
 a) a nucleic acid encoding SOCS1; and simultaneously or subsequently
 b) said at least one nucleic acid of interest encoding at least one polypeptide of interest;
wherein said steps are repeated at least once during culturing said cells.

Said at least one nucleic acid of interest and said nucleic acid encoding SOCS1 may be mRNAs, wherein each of said mRNAs may have a poly(A) tail at its 3'end comprising at least 200 adenines, at least 500 adenines, at least 1000 adenines, at least 1500 adenines, at least 2000 adenines, at least 2500 adenines, at least 3000 adenines, at least 3500 adenines, at least 4000 adenines, at least 4500 adenines, at least 4500 adenines, at least 5000 adenines, at least 5500 adenines or at least 6000 adenines.

Said at least step b) may be repeated at least three times, preferentially five times, wherein said poly(A) tail comprises at least 2000 adenines.

Said at least step b) may be repeated at least 8 times, wherein said poly(A) tail comprises at least 4000 adenines.

Both said nucleic acids may be provided as mRNA in the present method or alternatively, the nucleic acid encoding SOCS1 may be mRNA and the nucleic acid of interest encoding a polypeptide of interest may be DNA or vice versa.

In each of said mRNAs used in the present method 0% to 50%, preferentially 0% to 25% of the nucleobases uracil and/or cytosine of the mRNAs may be modified nucleobases.

More preferentially, said mRNAs used in the present method are unmodified mRNA. Modified mRNAs have been described to diminish the innate immunity of the transfected RNAs. Depending on the given application, higher modification rates are assumed to improve survival of cells even with repeated transfections. However, translation of modified mRNAs is diminished and therefore unmodified mRNAs will be preferred if repeated transfections can be achieved by other means than using modified nucleotides.

The period of repeating step a) and step b) or at least step b) may be one repeat between 4 hours to 48 hours, preferentially between 6 hours to 36 hours, more preferentially between 6 hours and 24 hours or the repeat may be daily.

Said cell may be a primary cell. Said cell may be a differentiated or somatic cell. Said cell may be an iPS cell or a stem cell. Said cell may be from a cell line Said at least one nucleic acid of interest may encode at least one reprogramming factor able to reprogram a primary cell or differentiated cell into an iPSC. Then the present method is used for reprogramming a primary cell or differentiated cell into an iPS cell.

Said at least one reprogramming factor may be selected from the group consisting of Oct3/4, c-myc, Sox2, Lin28, Klf4, and Nanog.

Said at least one nucleic acid of interest may be a differentiation factor able to trans-differentiate a somatic cell into a different cell type. Then the present method is used for trans-differentiation of a somatic cell into a different cell type.

Examples for such differentiation factors are MyoD, Gata4, Mef2c, Tbx5, Pdx1, Ngn3, MafA, Ascl1, Brn2, and Myt11.

In addition, said at least one nucleic acid of interest may be selected from the group consisting of DNA, mRNA, shRNA, siRNA, miRNA. Said nucleic acid of interest may be DNA, e.g. a plasmid encoding a gene of interest. Said nucleic acid of interest may be nucleic acid sequence encoding a chimeric antigen receptor (CAR).

Said cell may be an immune cell, e.g. a T cell.

Said method may be performed in a closed system.

Said method performed in a closed system may be an automated method.

An example for a closed system is the CLINIMACS PRODIGY® (an automated cell processing device; Miltenyi Biotec GmbH, Germany, WO2009/072003).

In a further aspect the invention provides a method of electroporation of a cell with at least one nucleic acid of interest, e.g. in a cell culture medium, comprising the steps of adding to the cell (or to the medium)
 a) a nucleic acid encoding SOCS1, and simultaneously or subsequently
 b) said at least one nucleic of interest.

Said nucleic acid encoding SOCS1 may be SOCS1 mRNA or DNA, e.g. a plasmid encoding the SOCS1. Preferentially, said nucleic acid encoding SOCS1 may be SOCS1 mRNA. Said nucleic acid encoding SOCS1 may be SOCS1 mRNA, wherein in said mRNA 0% to 50% of the nucleobases uracil and/or cytosine may be modified nucleobases, preferentially, wherein in said mRNA 0% to 25% of the nucleobases uracil and/or cytosine may be modified nucleobases, more preferentially wherein said mRNAs may be unmodified mRNA.

If said nucleic acid of interest is also mRNA, then said mRNA is a mRNA wherein in said mRNA 0% to 50% of the nucleobases uracil and/or cytosine may be modified nucleobases, preferentially, wherein in said mRNA 0% to 25% of the nucleobases uracil and/or cytosine may be modified nucleobases, more preferentially wherein said mRNAs may be unmodified mRNA.

Said at least one nucleic acid of interest and said nucleic acid encoding SOCS1 may be mRNAs, wherein each of said mRNAs may have a poly(A) tail at its 3'end comprising at least 200 adenines, at least 500 adenines, at least 1000 adenines, at least 1500 adenines, at least 2000 adenines, at least 2500 adenines, at least 3000 adenines, at least 3500 adenines, at least 4000 adenines, at least 4500 adenines, at least 4500 adenines, at least 5000 adenines, at least 5500 adenines or at least 6000 adenines.

Both said nucleic acids may be provided as mRNA in the present method or alternatively, the nucleic acid encoding SOCS1 may be mRNA and the nucleic acid of interest encoding a polypeptide of interest may be DNA or vice versa.

In addition, said at least one nucleic acid of interest may be selected from the group consisting of DNA, mRNA, shRNA, siRNA, miRNA. Said nucleic acid of interest may be DNA, e.g. a plasmid encoding a gene of interest. Said nucleic acid of interest may be nucleic acid sequence encoding a chimeric antigen receptor (CAR).

Said cell may be an immune cell, e.g. a T cell.

Said method may be performed in a closed system.

Said method performed in a closed system may be an automated method.

An example for a closed system is the CLINIMACS PRODIGY® (an automated cell processing device; Miltenyi Biotec GmbH, Germany, WO2009/072003).

The SOCS1 nucleic acid may be replaced by another member of the SOCS1 family having similar properties compared to SOCS1 protein, e.g. SOCS3 and CIS (Liang et al. Eur. J. Immunol. 2014. 44: 1265-1275) which also inhibit the activation of the JAK/STAT signaling pathways.

Definitions

Unless defined otherwise, technical and scientific terms used herein have the same meaning as commonly understood by one of ordinary skill in the art to which this invention belongs.

The term "nucleic acid" is the overall name for deoxyribonucleic acid (DNA) and ribonucleic acid (RNA). Nucleic acids (nucleic acid sequences) are linear polymers of nucleotides. Each nucleotide consists of three components: a purine or pyrimidine nucleobase (base), a pentose sugar, and a phosphate group. The substructure consisting of a nucleobase plus sugar is termed a nucleoside. Nucleic acid types differ in the structure of the sugar in their nucleotides—DNA contains 2'-deoxyribose while RNA contains ribose. Also, the nucleobases found in the two nucleic acid types are different: adenine, cytosine, and guanine are found in both RNA and DNA, while thymine occurs in DNA and uracil occurs in RNA.

Apart from adenine (A), cytosine (C), guanine (G), thymine (T) and uracil (U), DNA and RNA also may contain bases that have been modified. In DNA, the most common modified base is 5-methylcytosine ($m^5C$). In RNA, there are many modified bases, including those contained in the nucleosides pseudouridine (Ψ), dihydrouridine (D), inosine (I), and 7-methylguanosine ($m^7G$).

The term "modified ribonucleoside" refers to a ribonucleoside other than the standard guanine (G), adenine (A), cytidine (C), and uridine (U) nucleosides. Such modifications can occur naturally e.g. by post-transcriptional modifications to mammalian cell mRNA. For in vitro transcribed mRNA, also synthetic nucleotides can be used to produce modified RNAs. Modified nucleoside are preferentially 5'-methylcytidine and/or pseudouridine. Other nucleosides, that can be used, but are not limited to, are N6-methyladenosine (m6A), 3,2'-0-dimethyluridine (m4U), 2-thiouridine (s2U), 2' fluorouridine, 2'-0-methyluridine (Um), 2'deoxy uridine (2' dU), 4-thiouridine (s4U), 5-methyluridine (m5U), 2'-0-methyladenosine (m6A), N6,2'-0-dimethyladenosine (m6Am), N6,N6,2'-0-trimethyladenosine (m62Am), 2'-0-methylcytidine (Cm), 7-methylguanosine (m7G), 2'-0-methylguanosine (Gm), N2,7-dimethylguanosine (m2,7G), N2, N2, 7-trimethylguanosine (m2,2,7G), and inosine (I). Polyadenylation is the addition of a poly(A) tail to an RNA, preferentially messenger RNA (mRNA). The poly(A) tail consists of multiple adenosine monophosphates; in other words, it is a stretch of RNA that has only adenine bases. In eukaryotes, polyadenylation is part of the process that produces mature messenger RNA (mRNA) for translation. It, therefore, forms part of the larger process of gene expression. Normally, the eukaryotic mRNA contains a 5' cap. This 5' cap (also termed an RNA cap, an RNA 7-methylguanosine cap, or an RNA $m^7G$ cap) is a modified guanine nucleotide that has been added to the "front" or 5' end of a eukaryotic messenger RNA shortly after the start of transcription. The 5' cap consists of a terminal 7-methylguanosine residue that is linked through a 5'-5'-triphosphate bond to the first transcribed nucleotide. Its presence is critical for recognition by the ribosome and protection from RNases. The mRNAs described herein and used in the present invention have a 5' cap. Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. The 5'-terminal nucleoside is typically a guanosine, and is in the reverse orientation to all the other nucleotides, i.e., G(5')ppp(5')GpNpNp. Besides of using an enzymatic reaction to introduce the CAP structure to in vitro transcribed RNA, CAP analogs can be used to introduce the CAP structure already during the in vitro transcription.

Such CAP analog can be a so called Anti-Reverse Cap Analog ("ARCA"), in which the 2' or 3' OH group has been replaced with —OCH$_3$.

The terms "encoding" or "coding for" can be used interchangeably. "Encoding" as used herein refers to the property of specific sequences of nucleotides in a polynucleotide, such as a gene, a cDNA, or an mRNA, to serve as templates for synthesis of other macromolecules such as a defined sequence of amino acids. Thus, a gene encodes a protein if transcription and translation of mRNA corresponding to that gene produces the protein in a cell or other biological system. A "nucleic acid (sequence) encoding a polypeptide" includes all nucleotide sequences that are degenerate versions of each other and that code for the same amino acid sequence.

The term "expression" as used herein is defined as the transcription and/or translation of a particular nucleotide sequence driven by its promoter in a cell.

Suppressor of cytokine signaling 1 is a protein that in humans is encoded by the SOCS1 gene (SOCS1). This gene encodes a member of the STAT-induced STAT inhibitor (SSI), also known as suppressor of cytokine signalling (SOCS), family. SSI family members are cytokine-inducible negative regulators of cytokine signaling. The expression of this gene can be induced by a subset of cytokines, including IL2, IL3 erythropoietin (EPO), GM-CSF, and interferon-gamma (IFN-γ). The protein encoded by this gene functions downstream of cytokine receptors, and takes part in a negative feedback loop to attenuate cytokine signaling. The term "nucleic acid encoding SOCS1" as used herein refers to any nucleic acid (sequence) which encodes a complete SOCS1 protein or functional fragment thereof when transcription and/or translation of mRNA corresponding to that gene is performed in a cell.

It has been shown that SOCS1 peptides can replace functional SOCS1 full length protein (He, C et al, J Autoimmun. 2015)

The nucleic acid encoding SOCS1 may be a nucleic acid sequence derived from a mammal such as human, mouse, rat or sheep (e.g. an mRNA encoding mammal SOCS1), preferentially, the nucleic acid encoding SCOS1 is a human sequence of SOCS1 (e.g. an mRNA encoding human SOCS1).

The term "nucleic acid of interest" as used herein refers to any nucleic acid, nucleic acid sequence or nucleic acid polymer which is intended to be co-introduced together with the nucleic acid encoding SOCS1 into a cell. Said nucleic acid of interest may be a DNA molecule, e. g. gene of interest or a RNA molecule such mRNA, shRNA, siRNA, or miRNA. If the nucleic acid of interest is DNA or mRNA encoding a polypeptide of interest then the wording "nucleic acid of interest encoding a polypeptide of interest" may also be used herein. Said polypeptide may be a full-length protein or functional fragments thereof.

The term "co-introducing" as used herein refers to the intention of introducing several nucleic acids (the nucleic acid encoding SOCS1 and at least one nucleic acid of interest) into a cell. Several physical or chemical or biological methods are well known in the art for introducing nucleic acids into a cell, such as electroporation or lipofection or transfection by chemical compounds or viral transduction.

It is sufficient that the nucleic acid encoding SOCS1 is co-introduced into the cell with at least one nucleic acid of interest in one transfection of the at least once repeated transfections (several transfections) as long as the nucleic acid encoding SOCS1 is present and translated into the SOCS1 protein in the cell during further transfections with the nucleic acids of interest. In one embodiment of the invention, the nucleic acids are introduced within one transduction or transfection. In another embodiment of the invention the nucleic acid encoding SOCS1 can also be introduced separately e.g. before or after introducing the at least one nucleic acid of interest into a cell as long as the at least two nucleic acids are present in the cell within the same time for at least 72 h, 48 h, 36 h, 24 h, 18 h, 12 h, 6 h, 4 h, 2 h or 1 h. The term "simultaneous(ly)" in the context of adding the several nucleic acids to the medium in the method as disclosed herein has the same meaning as "co-introducing", therefore the addition of the several nucleic acids to the cell medium successively (but within one transduction or transfection or electroporation process) is also encompassed by the term "simultaneous(ly)".

Transfection is the process of deliberately introducing nucleic acids into cells. The term "repeated transfection" as used herein refers to the transfection of the same cell(s), e.g. in a cell culture medium, more than once. To repeatedly transfect a cell during the culturing of the cell the nucleic acids to be transfected have to be added repeatedly to the cell or the cell medium. In the method as disclosed herein the period (duration) of repeating the steps of addition to the cell or the cell medium
  a) a nucleic acid encoding SOCS1, and simultaneously or subsequently
  b) at least one nucleic acid encoding at least one polypeptide of interest;
wherein at least step b) is repeated at least once,
may be one repeat between 4 hours to 48 hours, preferentially between 6 hours to 36 hours, more preferentially between 6 hours and 24 hours or daily. But generally, any duration (or period) between to transfection processes may be chosen.

Several kind of transfection reagents are well known in the art and may be commercially available such as e.g. LIPOFECTIN® Reagent (a 1:1 (w/w) liposome formulation of the cationic lipid N-[1-(2,3-dioleyloxy) propyl]-n,n,n-trimethylammonium chloride (DOTMA) and dioleoyl phosphatidylethanolamine (DOPE) in membrane filtered water; Thermo Fisher Scientific Inc) or others. Transfection reagents include but are not limited to polycationic compounds (like Polyethylenimine (PEI), poly-L-lysine or DEAE-Dextrane), chemical compounds like Calcium phosphate or liposomal formulations containing charged lipids and polymers (lipe DOTAP [N-[1-(2,3-dioleoyloxy) propyl]-N,N,N-trimethylammonium methyl sulfate], 1,2-di-O-octadecenyl-3-trimethylammonium propane (DOTMA) and combinations thereof, e.g. LIPOFECTAMINE™ is a 3:1 (w/w) mixture of the polycationic lipid, 2,3-dioleyloxy-N-[2 (sperminecarboxamido) ethyl]-N,N-dimethyl-1-propan-aminium trifluoroacetate (DOSPA), and DOPE. The nucleic acid encoding SOCS1 and the at least one nucleic acid of interest may be delivered into a cell by using a transfection reagent as described above or by using any transfection reagent known to the skilled person and suitable for transfecting a cell.

The term efficiency of transfection as used herein includes the aspects of expression levels of the nucleic acids of interest and/or the overall cell survival and/or transfection rate.

The term electroporation is the process of applying an electric field to cells, thereby disturbing the integrity of the cell membrane, and allowing molecules like nucleic acids to enter the cells. Loosing cell membrane integrity can be lethal to cells and electroporation conditions have to be balanced between transfection efficiency and cell survival. Improving cell survival by introducing SOCS1 nucleic acid into the cells allows higher transfection rates to be achieved.

The term enhanced efficiency or enhancing efficiency describes the fact that over cell survival is improved and/or expression levels are enhanced and/or transfection rate is improved.

The term "cell culture medium" as used herein includes liquids providing the chemical conditions which are required for cell maintenance. Examples of chemical conditions which may support cell expansion include but are not limited to solutions, buffers, serum, serum components, nutrients, vitamins, cytokines and other growth factors which are regularly provided in (or may be given manually to) the cell culture medium. Media suitable for use to cultivate cells and those for special applications e.g. special medium for reprogramming of primary cells to induced pluripotent stem cells are known in the art As used herein the term "culturing" includes providing the chemical and physical conditions (e.g., temperature, gas) which are required for cell maintenance, and growth factors. Often culturing the cells includes providing the cells with conditions for expansion (proliferation). Examples of chemical conditions which may support cell expansion include but are not limited to buffers, serum, nutrients, vitamins, antibiotics, cytokines and other growth factors which are regularly provided in (or may be given manually to) the cell culture medium suited for cell expansion. Media for maintenance and/or expansion of cells are well-known in the art. Cells that are cultured directly from a subject are known as primary cells. With the exception of some derived from tumors, most primary cell cultures have limited lifespans.

A somatic cell is any biological cell forming the body of an organism; that is, in a multicellular organism, any cell other than a gamete, germ cell, gametocyte or undifferentiated stem cell.

The term "reprogramming factor(s)" as used herein, refers to one or more biologically active polypeptides or nucleic acids encoding them or small molecules that act on a cell to alter transcription, and which upon expression, reprogram a somatic cell to a different cell type, or to multipotency or to pluripotency.

Induced pluripotent stem cells (also known as iPS cells or iPSCs) are a type of pluripotent stem cell that can be generated directly from newborn and adult primary cells. iPSCs are typically derived by introducing a specific set of pluripotency-associated genes, or "reprogramming factors", into a given cell type. The original set of reprogramming factors (also dubbed Yamanaka factors) are the genes Oct4 (Pou5f1), Sox2, cMyc, and Klf4. While this combination is most conventional in producing iPSCs, each of the factors can be functionally replaced by related transcription factors, miRNAs, small molecules, or even non-related genes such as lineage specifiers. The reprogramming mixture can also be amended by more reprogramming factors to improve efficiency of reprogramming.

Differentiation factors are often transcription factors which promote the differentiation of a more pluripotent cell such as an embryonic stem cell or iPSC into a less pluripotent cell such as a differentiated cell like a fibroblast cell, neuronal cell or a cardiomyocyte. But differentiation factors can also be transcription factors which promote the differentiation from a differentiated cell into another cell differentiated cell type (trans-differentiation).

The term "trans-differentiation" is also known as lineage reprogramming. It is a process where one mature somatic cell transforms into another mature somatic cell without undergoing an intermediate pluripotent state or progenitor cell type.

The term "closed system" as used herein refers to any closed system which reduces the risk of cell culture contamination while performing culturing processes such as the introduction of new material and performing cell culturing steps such as proliferation, differentiation, activation, genetic modification and/or separation of cells. Such a system allows to operate under GMP or GMP-like conditions ("sterile") resulting in cell compositions which are clinically applicable.

An example for a closed system is the CLINIMACS PRODIGY® (an automated cell processing device; Miltenyi Biotec GmbH, Germany, WO2009/072003).

The terms "automated method" or "automated process" as used herein refer to any process being automated through the use of devices and/or computers and computer software which otherwise would or could be performed manually by an operator. Methods (processes) that have been automated require less human intervention and less human time to deliver. In some instances a method is automated if at least one step of the method is performed without any human support or intervention. Preferentially the method is automated if all steps of the method are performed without human support or intervention.

EMBODIMENTS

In one embodiment of the invention, the nucleic acids of interest used in the method disclosed herein are e.g. nucleic acids encoding transcription factors (for example Oct3/4, c-myc, Sox2, Lin28, Klf4, Nanog) used for reprogramming of primary, differentiated cells (for example, but not limited to human fibroblasts, renal epithelial cells, endothelial cells, mesenchymal stem cells) into iPSCs. The nucleic acids of interest are provided as mRNAs and are delivered using a transfection reagent suitable for transfecting the to be reprogrammed cells. The addition of SOCS1 mRNA to the to be transfected mRNAs of interest prevents massive cell death due to innate immune activation caused by the repeated transfection of the mRNAs. The addition of SOCS1 mRNA can also enhance expression levels of the introduced mRNAs thereby increasing the efficiency of reprogramming of the primary cells. The addition of SOCS1 mRNA omits the need of addition of other immune suppressive compounds to the medium. Preferentially both the SOCS1 mRNA and the mRNA(s) of interest have a poly(A) tail comprising at least 1500, more preferentially at least 2000 adenines.

In one embodiment of the invention the mRNAs used in the herein described embodiments may bear modified nucleobases if the nucleic acids used are mRNA. In one embodiment of the invention 0% to 25% of the bases cytosine/uracil in the mRNAs used may be modified cytosines/uracils.

In one embodiment of the invention the nucleic acids of interest used in the method disclosed herein are e.g. transcription factors (for example Oct3/4, c-myc, Sox2, Lin28, Klf4, Nanog) used for reprogramming of primary, differentiated cells (for example, but not limited to human fibroblasts, renal epithelial cells, endothelial cells, mesenchymal stem cells) into iPSCs. The nucleic acids of interest are provided as DNA, e.g. within an episomal plasmid, and are delivered using a transfection reagent suitable for transfecting the to be reprogrammed cells. The addition of SOCS1 mRNA during the transfection process prevents massive cell death due to innate immune activation caused by the exogenously added DNA. The addition of SOCS1 mRNA can also enhance expression levels of the introduced DNA plasmids thereby increasing the efficiency of reprogramming of the primary cells. The addition of SOCS1 mRNA omits the need of addition of other immune suppressive compounds to the medium. Preferentially the SOCS1 mRNA has a poly(A) tail comprising at least 1500, more preferentially at least 2000 adenines.

In one embodiment of the invention the nucleic acids of interest used in the method disclosed herein are e.g. transcription factors (for example Oct3/4, c-myc, Sox2, Lin28, Klf4, Nanog) used for reprogramming of primary, differentiated cells (for example, but not limited to human fibroblasts, renal epithelial cells, endothelial cells, mesenchymal stem cells) into iPSCs. The nucleic acids of interest may be provided as mRNA or as DNA, e.g. within a plasmid, and are delivered using e.g. transfection reagent suitable for transfecting the to be reprogrammed cells. The addition of DNA encoding SOCS1 during the transfection process prevents massive cell death due to innate immune activation caused by the exogenously added mRNA or DNA. The addition of the DNA encoding SOCS1 can also enhance expression levels of the introduced DNA plasmids which harbor the nucleic acids of interest thereby increasing the efficiency of reprogramming of the primary cells. The addition of the DNA encoding SOCS1 omits the need of addition of other immune suppressive compounds to the medium. When the nucleic acids of interest are mRNAs then preferentially the mRNAs of interest have a poly(A) tail comprising at least 1500, more preferentially at least 2000 adenines.

In one embodiment of the invention the nucleic acids of interest is one or more transcription factors necessary for trans-differentiation of a somatic cell into a different cell type, e.g. repeated transfection of a fibroblast into skeletal muscle cells with MyoD mRNA or DNA encoding MyoD. Trans-differentiation can also be achieved by using repeated transfection and is accompanied by activation of innate immune pathways counteracting the trans-differentiation efforts by inducing cell death or activating unwanted cell signaling pathways. In the art, addition of B18R protein is used to suppress activation of innate immune pathways. The addition of a nucleic acid encoding SOCS1 such as SOCS1 mRNA during the transfection process prevents massive cell death due to innate immune activation caused by the repeated transfection of the mRNAs. The addition of the nucleic acid encoding SOCS1 such as SOCS1 mRNA can also enhance expression levels of the introduced mRNAs or DNAs thereby increasing the efficiency of trans-differentiation of the somatic cell into a different cell type. When mRNA is used, then preferentially both the SOCS1 mRNA and the mRNA(s) of interest have a poly(A) tail comprising at least 1500, more preferentially at least 2000 adenines.

In one embodiment of the invention the addition of SOCS1 mRNA as disclosed herein can also be used to enhance the effects of adding neuronal transcription factors to a cell (e.g. fibroblasts) for trans-differentiation of the cell into neuronal cells or their progenitor cells by introducing specific transcription factors into said cell, e.g. Ascl1, Brn2, NeuroD1 and/or Myt1l). The SOCS1 mRNA can also be used to trans-differentiation to cell (e.g. fibroblasts) into cardiomyocyte cells by introduction of various transcription factors (e.g. GATA4, Mef2c, Tbx5).

In one embodiment of the invention the nucleic acids of interest are delivered to the cell by electroporation using electroporation procedures known in the art. The nucleic acids of interest are delivered either as mRNA or DNA with the said SOCS nucleic acid either as mRNA or DNA by adding the nucleic acids to cells and applying an electric field to disrupt the cell membrane and enable nucleic acids to enter the cells. The use of SOCS1 nucleic acids is preferred for cells with effective innate immune reactions against foreign nucleic acids. For example it is well known in the art that massive cell death occurs after electroporation of plasmid DNA to T cells.

In one embodiment of the invention the addition of SOCS1 mRNA is used for the delivery of mRNA, shSNA, miRNA, siRNA, or plasmid DNA that might be toxic to the cells to enhance cell survival. The potentially toxic nucleic acid might also be applied subsequently to the SOCS1 nucleic acid to allow translation of the SOCS1 protein or fragment and suppression of cytokine secretion before the potentially toxic nucleic acid enters the cells. As repeated transfections are tedious and accompanied by cell stress In an preferred embodiment, the electroporation is performed in a closed system.

EXAMPLES

Hereinafter, the present invention is described in more detail and specifically with reference to the examples, which however are not intended to limit the present invention.

Example 1: GFP Expression in the Presence of SOCS1 mRNA

SOCS1 and B18R mRNA was generated by in vitro transcription using T7 Polymerase (Miltenyi Biotec GmbH) in the presence of the modified nucleotides pseudouridine and 5-methylcytidine. The in vitro transcribed mRNA was capped using the vaccinia virus capping enzyme (New England Biolabs, Inc.). A polyA tail was added using the yeast polyA polymerase (Affymetrix, Thermo Fisher Scientific). The polyA tail of SOCS1 and B18R mRNA contained approx. 1500 adenine bases. GFP mRNA was generated similarly except that only unmodified nucleotides were used for transcription and that the polyA tail contained at least 3000 nucleotides (nt). Human newborn foreskin fibroblasts (BJ) were transfected with in vitro transcribed GFP in the presence of increasing amounts of B18R or SOCS1 mRNA using the STEMMACS™ mRNA transfection kit (a lipid-based transfection system; Miltenyi Biotec GmbH) according to the suppliers instructions. Medium was changed 4 h after transfection. For controls, GFP mRNA was transfected without addition of SOCS1 or B18R mRNA and in the presence or absence of B18R protein (eBioscience).

The fibroblasts were transfected daily for 3 days. At day 4, single cell suspensions were subjected to flow cytometric analysis determining cell viability (using propidium iodide), GFP expression levels (FITC-Mean) and % positive cells (gated on propidium iodide negative cells).

Daily transfection with GFP mRNA alone resulted in a low GFP expression level which could be significantly increased in the presence of SOCS1 mRNA but not in the presence of B18R mRNA although with B18R protein (FIG. 1). The MFI of cells co-transfected with GFP and SOCS1 mRNA is higher compared to cells co-transfected with GFP and B18R mRNA and comparable to cells only transfected with GFP mRNA. The MFI is close to MFI of cells transfected 3 times with GFP mRNA only but in the presence of B18R protein.

This experiment shows that despite the anti-viral activity of B18R protein, B18R mRNA is not able to rescue the cells from activation of innate immunity. Induction of innate immune responses results in a decreased GFP expression level. SOCS1 mRNA is able to increase the GFP expression levels significantly.

Figure 2:
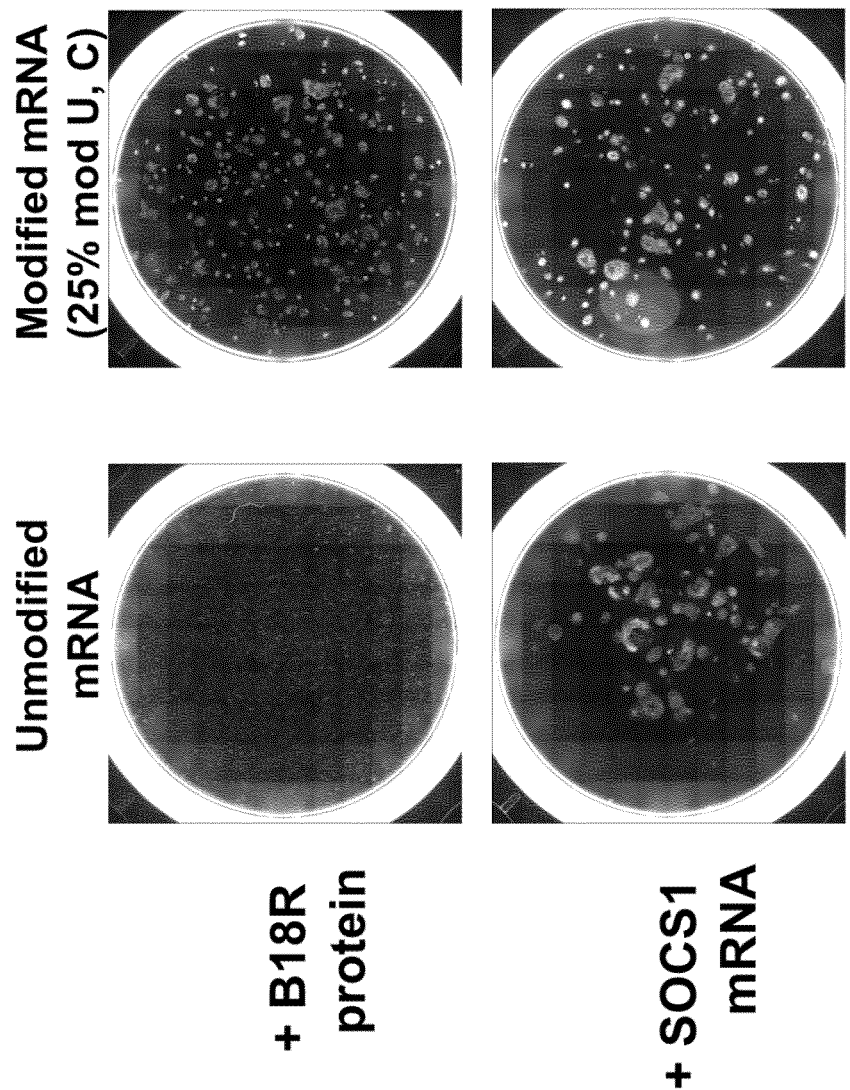
FIG. 2: Comparison of the effects of B18R and SOCS1 mRNA for the generation of iPSCs using mRNA transfection

Example 2: Reprogramming Fibroblasts into Induced Pluripotent Stem Cells Using SOCS1 mRNA Human newborn foreskin fibroblasts (BJs) were plated in different cell densities and transfected using a mRNA mixture containing Oct4:Sox2:Klf4:Lin28:c-Myc:Nanog: nuclear eGFP (all mRNAs contained polyA tails >2000 nt). The cells were transfected using a shortened reprogramming protocol with 2 daily transfections (6 h interval) for 5 consecutive days. Medium was exchanged immediately before transfection. In one condition, the medium was supplemented with B18R protein as used in published protocols (200 ng/ml), in the other condition, SOCS1 mRNA containing polyA tail >2000 nt was added to the mixtures of mRNAs and transfected simultaneously. Generated iPSCs were identified at d14 (13 days after first transfection) by intracellular staining of the iPSC colonies using Oct3/4 which is a pluripotency marker. Number and size of the generated iPSCs was higher in case of cells transfected with SOCS1 mRNA compared to use of B18R protein (see FIG. 2).

Figure 3:
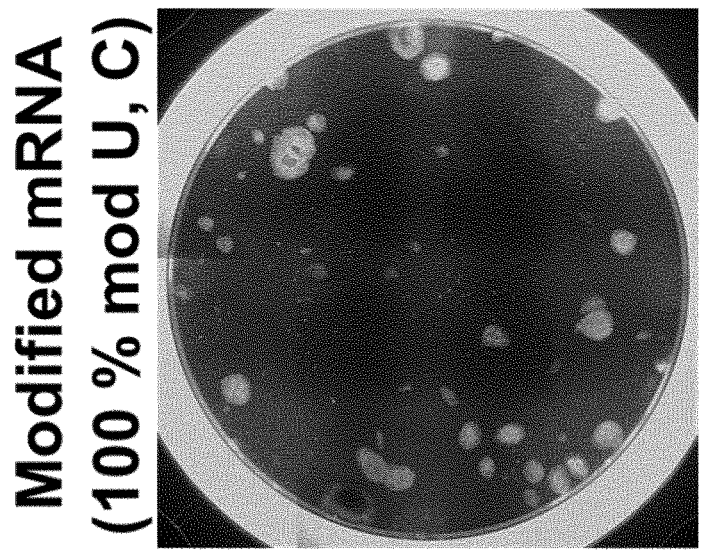
FIG. 3: Effects of modified and unmodified mRNA for reprogramming human newborn foreskin fibroblasts into iPSCs.
Figure 3:
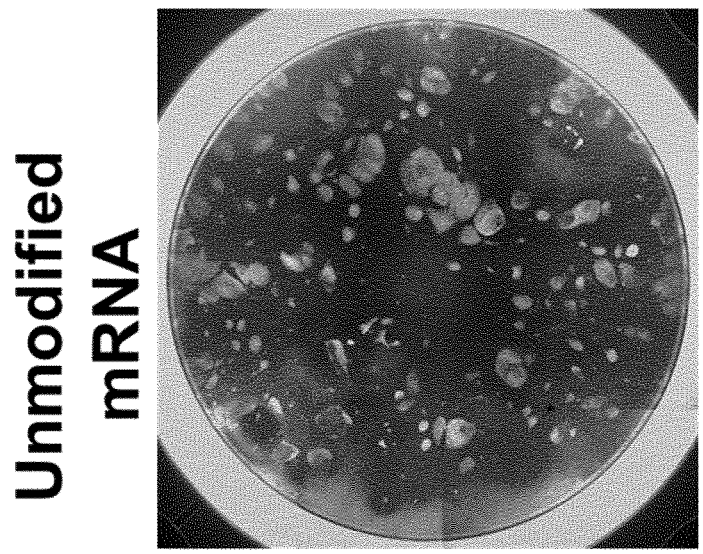

Example 3: Reprogramming of Fibroblasts into Induced Pluripotent Stem Cells Using Unmodified or 25% Modified mRNA Human newborn foreskin fibroblasts were plated on Matrigel coated plates and transfected with mRNA mixtures containing either modified mRNA (75% uridine and 25% pseudouridine, 75% cytidine and 25% 5-methylcytidine used in the in-vitro transcription to produce the RNA) or unmodified mRNA with polyA tails >2000 nt. Both mixtures contained SOCS1 mRNA The iPSC colonies were generated using a newly developed protocol using two daily transfections for 5 days with medium exchanges before each transfection. First colonies could be detected at d10 and stained at d14 (13 days after first transfection). The colonies were identified by intracellular staining using Oct 3/4 as a pluripotency marker. Efficiency of iPSCs generation is significantly enhanced when unmodified mRNA is used (see FIG. 3).

Example 4: Effect of Length of Poly(A) on Reprogramming Efficiency

Figure 4:
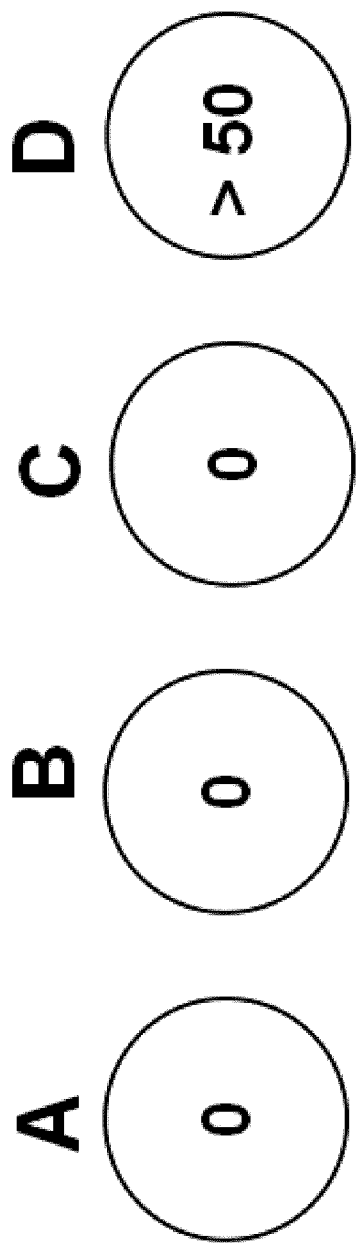
FIG. 4: Effects of the length of poly A tail for the successful reprogramming of fibroblasts into iPSCs

Human newborn foreskin fibroblasts were plated on Matrigel coated plates and transfected with mRNA mixtures containing 25% modified mRNA (75% uridine and 25% pseudouridine, 75% cytidine and 25% 5-methylcytidine used in the in-vitro transcription to produce the RNA) and a poly(A) tail shorter than 2000 nt or longer than 2000 nt. To all mixtures containing the mRNA of reprogramming factors SOCS1 mRNA was added. The iPSC colonies were generated using a newly developed protocol using two daily transfections for 5 days with medium exchanges before each transfection. First colonies could be detected at d10 and stained at d14 (13 days after first transfection). The colonies were identified by intracellular staining using Oct 3/4 as a pluripotency marker. Only the mixtures containing poly(A) >2000 nt of both kinds of mRNA (Reprogramming factors and SOCS1 mRNA) gave rise to iPSC colonies when transfection was performed ten times (see FIG. 4).

Example 5: Effect of Length of Poly(A) on GFP Expression

Figure 5:
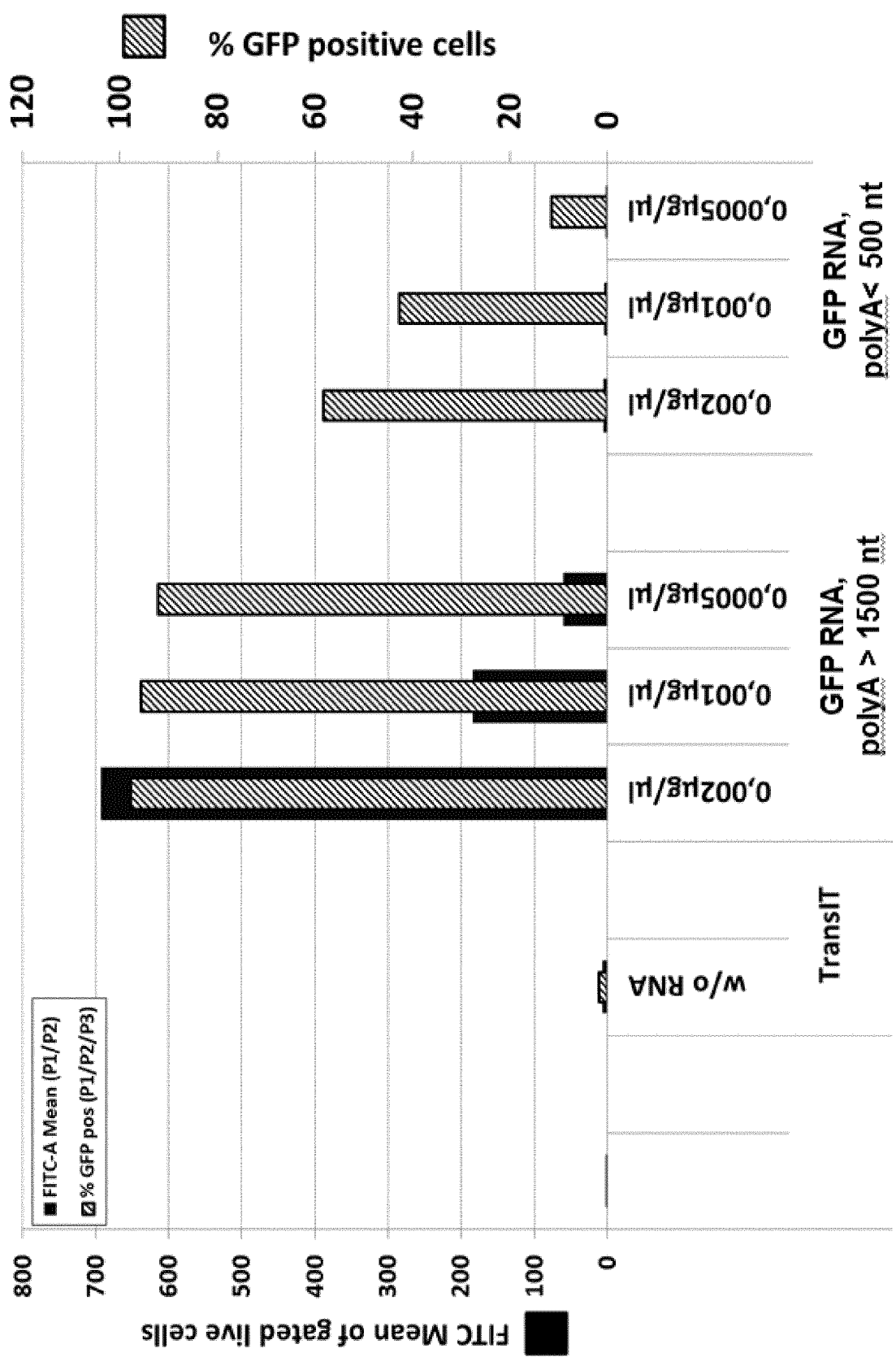
FIG. 5: Effect of the length of polyA tail for expression of the GFP protein

HeLa cells were plated and transfected with GFP mRNA containing either a short poly(A) tail (<500 nt) or a long poly(A) tail (>500 nt) using TransIT transfection reagent (Lifetechnologies). Cells were cultivated for 24 h and harvested for quantification using flow cytometric assessment. Transfection of GFP mRNA with long poly(A) tails yielded in higher percentage of transduced cells and in higher GFP expression levels as indicated by a higher mean fluorescence index (MFI) (see FIG. 5).

Example 6: Effect of SOCS1 mRNA on the Cell Vitality and Transfection Rate after Electroporation of eGFP Plasmid DNA into T Cell Human T cells were isolated from peripheral blood mononuclear cells (PBMC) using the pan T cell isolation kit, human (Miltenyi Biotec). Isolated T cells were seeded in 48-well plates at $1.9 \times 10^6$ cells in 0.5 ml TEXMACS™ medium (serum-free cell culture medium; Miltenyi Biotec) supplemented with PROLEUKIN® S (Il2) at a final concentration of 20 ng/ml (The $ED_{50}$ is ≤0.3 ng/mL* corresponding to a specific activity of ≥$3.0 \times 10^6$ IU/mg (calibrated with NIBSC 86/504) or ≥$1 \times 10^7$ IU/mg (calibrated with PROLEUKIN®)) and penicillin-streptomycin at a final concentration of 50 to 100 I.U./ml penicillin and 50 to 100 µg/ml streptomycin and cultivated at 37° C. and 5% $CO_2$. Three days before electroporation, T cells were activated using MACS® GMP TRANSACT™ CD3/CD28 Kit (polymeric nanomatrix conjugated to recombinant humanized CD3 and CD28 agonist; Miltenyi Biotec) at recommended titer of 1:200 (MACS® GMP TRANSACT™ CD3 Reagent and 1:400 (MACS® GMP TRANSACT™ CD28 Reagent). After 3 days of cultivation at 37° C. and 5% $CO_2$, T cells were harvested and centrifuged for 10 minutes at 300×g. Cells were resuspended in PBS and again centrifuged at 300×g. Cells were resuspended at $10^7$ cells/ml in 100 µl buffer M (5 mM KCl; 15 mM MgCl2; 120 mM $Na_2HPO_4$/$NaH_2PO_4$ PH7.2; 50 mM Manitol). The cell suspension was mixed with 2 µg eGFP encoding plasmid without (control) or mixed with 0.5 µg Socs1 mRNA comprising either a poly-A tail of about 1400 nucleotides length or of about 4800 nucleotides length respectively and immediately transferred to an electroporation cuvette. The SOCS1 mRNA comprised only unmodified nucleotides i.e. Adenosin, Guanin, Cystosin, Uracil.

T cells were electroporated on a NUCLEOFECTOR™ Device (Lonza) using the program T-023. After electroporation, cells were immediately transferred to an 48 well-plate containing 0.5 ml TEXMACS™ medium (Miltenyi Biotec) supplemented with PROLEUKIN® S (Il2) at a final concentration of 20 ng/ml (The $ED_{50}$ is ≤0.3 ng/ml corresponding to a specific activity of ≥$3.0 \times 10^6$ IU/mg (calibrated with NIBSC 86/504) or ≥$1 \times 10^7$ IU/mg (calibrated with PROLEUKIN®)) and penicillin-streptomycin at a final concentration of 50 to 100 I.U./ml penicillin and 50 to 100 µg/ml streptomycin and cultivated for 2 days at 37° C. and 5% $CO_2$. T cells were harvested and centrifuged for 10 minutes at 300×g. For flow cytometric analysis, cells were resuspended in 40 µl PEB (phosphate buffered saline containing EDTA), 20 µl FCR-Block, and 50 µl antibody staining cocktail (CD4-VIOBLUE® (blue fluorochrome), CD8-VIOGREEN™ (green fluorochrome). CD25-PE, CD69-APC, CD3-APC07). After 10 minutes incubation at 4° C. in the dark, cells were centrifuged for 10 minutes at 300×g and resuspended in 0.5 ml PEB. Just before flow cytometric analysis, propidium iodide at a final concentration of 1 µg/ml was added. 25 µl cell suspension was analyzed on a MACSQUANT® flow cytometer.

Figure 6:
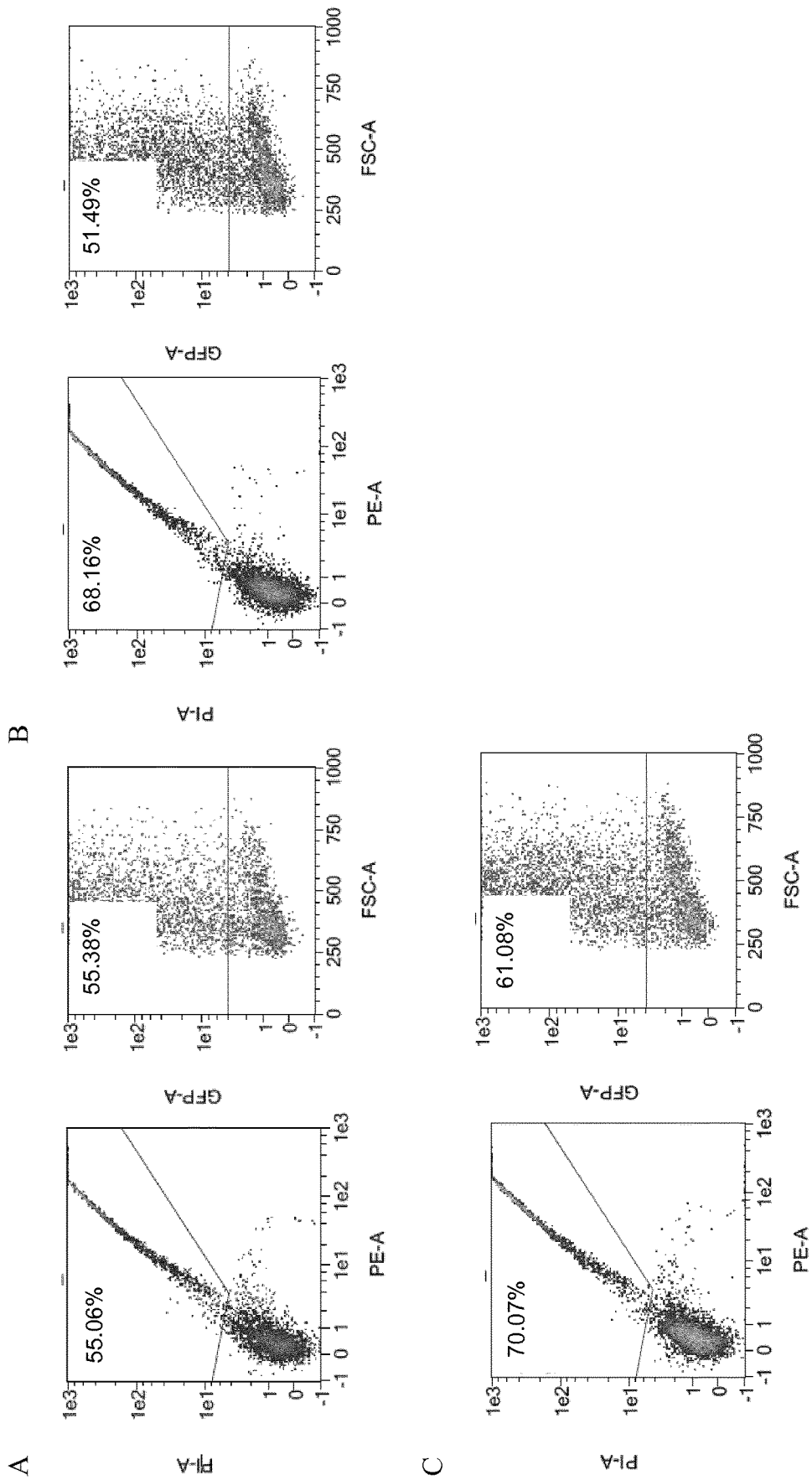
FIG. 6: Effect of SOCS1 mRNA on the cell vitality and transfection rate after electroporation of eGFP plasmid DNA into T cell (FIG. 6 A, B, C).

T cell viability was determined according to propidium iodide staining and eGFP expression was monitored by fluorescence detection in the APC channel. The control electroporation of eGFP plasmid without SOCS1 mRNA (FIG. 6A) resulted in 58% viable cells and 55% of the viable cells were eGFP positive. By co-electroporation of eGFP plasmid and SOCS1 mRNA comprising about 1400 nucleotides of poly-A, 68% of the cells were viable and 51% of the viable cells were eGFP positive (FIG. 6B). Surprisingly, by co-electroporation of eGFP plasmid and SOCS1 mRNA comprising about 4800 nucleotides poly-A, cell viability increased to 70% and also the proportion of eGFP positive cells within the viable cells increased to 61% (FIG. 6C).

Apparently, SOCS1 expression after the electroporation of the respective mRNA enhances survival of T cells electroporated with plasmid DNA. In addition, a longer poly-A tail used for the electroporated SOCS1 mRNA enhanced the transfection rate i.e. the proportion of cells expressing the gene of interest.

The invention claimed is:

1. An in vitro method of repeated transfection of a fibroblast cell with at least one mRNA encoding a reprogramming factor, comprising introducing to the fibroblast cell: a) Suppressor Of Cytokine Signaling 1 (SOCS1) mRNA; and simultaneously or subsequently b) the at least one mRNA encoding a reprogramming factor; wherein the step b) is repeated at least once, and wherein the SOCS1 mRNA and the at least one mRNA encoding the reprogramming factor have a poly (A) tail at its 3' end comprising at least 2000 adenines, respectively, wherein the reprogramming factor induces reprograming of the fibroblast cell into an induced pluripotent stem cell (iPSC), wherein the at least one mRNA encoding the reprogramming factor is an mRNA reprogramming mixture comprising mRNAs encoding for Oct3/4, Sox2, Klf4, Lin28, c-Myc, and Nanog.

2. The method according to claim 1, wherein the step b) is repeated at least three times.

3. The method according to claim 2, wherein the step b) is repeated within 4 hours to 48 hours between a first time and a second time.

4. The method according to claim 1, wherein the method results in an increased expression of the mRNA encoding the reprogramming factor compared to a corresponding method wherein the SOCS1 mRNA is not co-introduced.

5. The method according to claim 4, wherein the method results in an increased reprogramming efficiency of the fibroblast cell compared to a corresponding method wherein the SOCS1 mRNA is not co-introduced.

\* \* \* \* \*